US012727802B2

(12) United States Patent
Park et al.

(10) Patent No.: US 12,727,802 B2
(45) Date of Patent: Sep. 8, 2026

(54) SYSTEM, APPARATUS, AND METHOD FOR DETERMINING STRESS

(71) Applicant: ELECTRONICS AND TELECOMMUNICATIONS RESEARCH INSTITUTE, Daejeon (KR)

(72) Inventors: Kyoung Hyun Park, Daejeon (KR); Hyun Suk Kim, Daejeon (KR); Min Jung Kim, Daejeon (KR); Dae Sub Yoon, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 288 days.

(21) Appl. No.: 18/475,750

(22) Filed: Sep. 27, 2023

(65) Prior Publication Data

US 2024/0298944 A1 Sep. 12, 2024

(30) Foreign Application Priority Data

Mar. 7, 2023 (KR) ........................ 10-2023-0029979

(51) Int. Cl.
*A61B 5/16* (2006.01)
*G16H 10/20* (2018.01)

(52) U.S. Cl.
CPC ............. *A61B 5/165* (2013.01); *G16H 10/20* (2018.01)

(58) Field of Classification Search
CPC ..... A61B 5/165; A61B 5/7267; A61B 5/7275; G16H 10/20; G16H 50/70
See application file for complete search history.

(56) References Cited

U.S. PATENT DOCUMENTS

| | | | | |
|---|---|---|---|---|
| 10,789,961 | B2 | 9/2020 | Noh et al. | |
| 2014/0234815 | A1 | 8/2014 | Jang et al. | |
| 2021/0169415 | A1 * | 6/2021 | Kon .................. | A61B 5/02055 |
| 2023/0197274 | A1 | 6/2023 | Kim et al. | |

FOREIGN PATENT DOCUMENTS

| | | | | | |
|---|---|---|---|---|---|
| KR | 20170006919 | A | * | 1/2017 | ............ G06Q 50/22 |
| KR | 1020170028736 | | | 3/2017 | |
| KR | 1020200048027 | A | | 5/2020 | |
| KR | 1020210067827 | A | | 6/2021 | |
| KR | 1020220012066 | A | | 2/2022 | |
| KR | 102397225 | B1 | | 5/2022 | |
| KR | 102454737 | B1 | | 10/2022 | |
| WO | WO-2022208874 | A1 | * | 10/2022 | ............ G06Q 10/10 |
| WO | WO-2022215239 | A1 | * | 10/2022 | .............. A61B 5/16 |

OTHER PUBLICATIONS

Tervonen, J., et al., 'Personalized mental stress detection with self-organizing map: From laboratory to the field', Computers in Biology and Medicine, https://doi.org/10.1016/j.compbiomed.2020.103935, Jul. 29, 2020.

* cited by examiner

*Primary Examiner* — Carl H Layno
*Assistant Examiner* — Aya Ziad Bakkar
(74) *Attorney, Agent, or Firm* — Rabin & Berdo, P.C.

(57) ABSTRACT

Provided are a system, apparatus, and method for determining stress. The apparatus according to the present invention includes a communication interface and a processor connected to the communication interface, wherein the processor collects biometric data and survey data of a user through the communication interface, generates a personalized stress classification model on the basis of the biometric data and the survey data, and determines whether the user is stressed using the personalized stress classification model.

14 Claims, 9 Drawing Sheets

FIG. 8

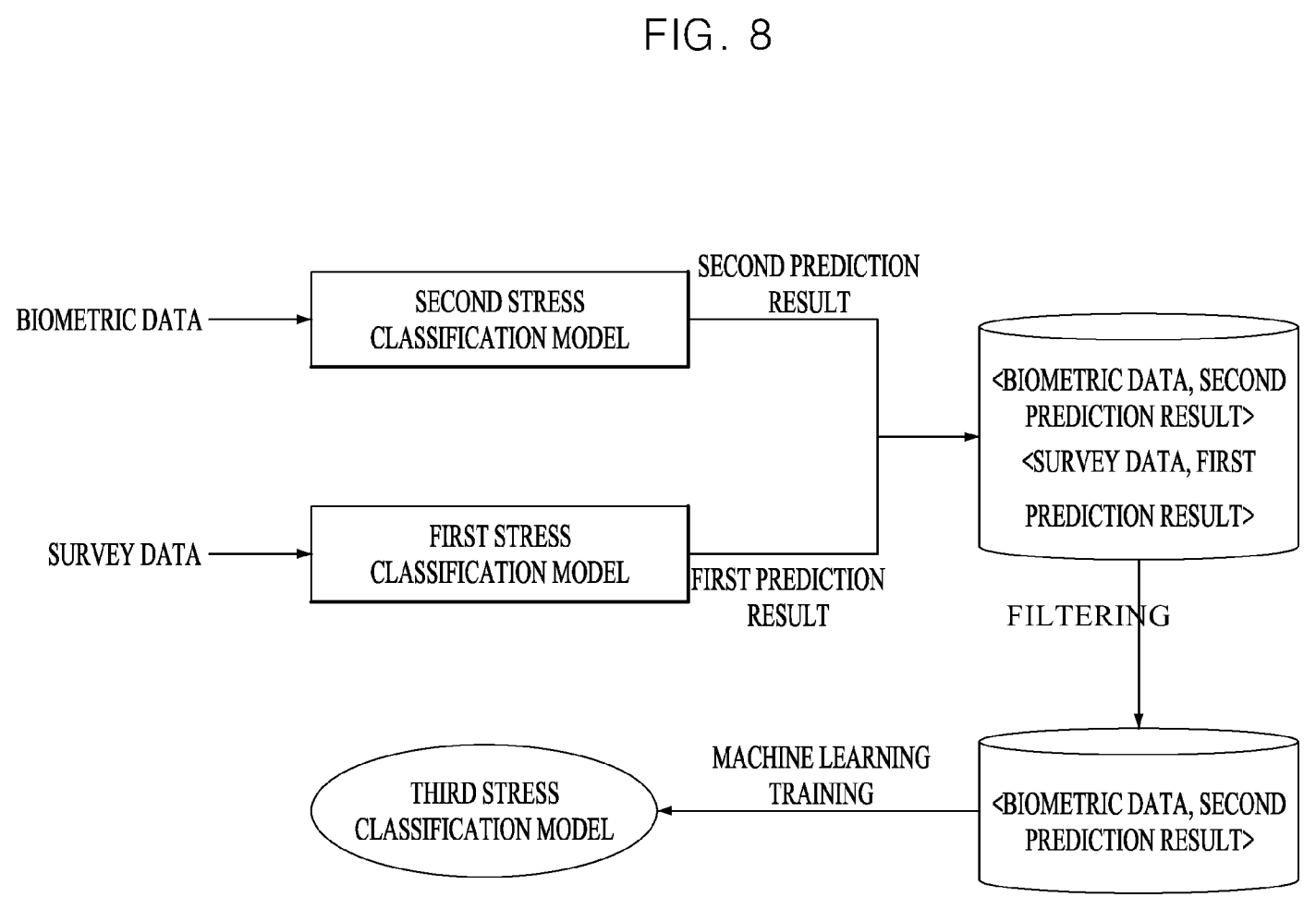

BIOMETRIC DATA

SURVEY DATA

SECOND STRESS CLASSIFICATION MODEL

FIRST STRESS CLASSIFICATION MODEL

SECOND PREDICTION RESULT

FIRST PREDICTION RESULT

<BIOMETRIC DATA, SECOND PREDICTION RESULT>
<SURVEY DATA, FIRST PREDICTION RESULT>

FILTERING

<BIOMETRIC DATA, SECOND PREDICTION RESULT>

MACHINE LEARNING TRAINING

THIRD STRESS CLASSIFICATION MODEL

SYSTEM, APPARATUS, AND METHOD FOR DETERMINING STRESS

CROSS-REFERENCE TO RELATED APPLICATION

This application claims priority to and the benefit of Korean Patent Application No. 2023-0029979 filed on Mar. 7, 2023, the disclosure of which is incorporated herein by reference in its entirety.

BACKGROUND

1. Field of the Invention

The present invention relates to a system, apparatus, and method for determining stress, and more specifically, to a system, apparatus, and method for determining whether a user is stressed.

2. Discussion of Related Art

Most people experience stress in their daily lives. Mild stress has a positive effect on increasing work productivity, but excessive stress can cause various problems and, in severe cases, lowers the quality of life. Therefore, it is necessary to detect such excessive stress at an early stage and manage the stress so that it does not develop into chronic stress.

Conventionally, an individual's stress was measured by conducting an interview or filling out a questionnaire. However, methods of analyzing stress through interviews had limitations in widespread use because the interviews had to be conducted by experts specializing in psychology. In order to overcome these limitations, a method of analyzing stress through questionnaires is generally used.

Meanwhile, recently, a method of analyzing an individual's stress using biometric signals has been developed and used. A method of analyzing stress using biometric signals is a method in which a person's biometric signals are collected and their stress is analyzed through a stress classification model that is generated using the collected biometric signals as training data. Since such a stress classification model is used to analyze stress on the basis of general people's characteristics, there is a problem in that when the stress classification model is applied to an individual, accuracy thereof may be lowered.

In addition, the method of analyzing stress using biometric signals focuses on determining physical stress, and thus has a problem in that psychological stress is not considered at all. When a stress of the same intensity is applied from the outside, a physical response pattern corresponding to the external stress may be similar for each person, but the actual acceptance of the external stress as stress may vary from person to person. That is, there may be a case where the external stress is recognized as physical stress but not recognized as psychological stress. Such a case may occur when objective stress and subjective stress are different from each other, and in order to accurately analyze the stress, it is necessary to consider not only the objective stress but also the subjective stress. However, in the conventional method of analyzing stress using biometric signals, subjective stress is not considered at all, and thus there is a problem of low accuracy.

The related art of the present invention is disclosed in Korean Laid-open Patent Publication No. 10-2021-0067827 (Published on Jun. 8, 2021).

SUMMARY OF THE INVENTION

The present invention is directed to providing a system, apparatus, and method for determining stress, in which a stress classification model optimized for a user may be generated using physical and psychological information collected from the user, and the optimized stress classification model may be used to determine whether the user is stressed, thereby improving the accuracy of stress determination for the user.

According to an aspect of the present invention, there is provided an apparatus for determining stress, which includes a communication interface, and a processor connected to the communication interface, wherein the processor collects biometric data and survey data of a user through the communication interface, generates a personalized stress classification model on the basis of the biometric data and the survey data, and determines whether the user is stressed using the personalized stress classification model.

The processor may generate a first stress classification model on the basis of the survey data, generate training data from the biometric data and the survey data using the first stress classification model and a pre-stored biometric data-based second stress classification model, and generate the personalized stress classification model on the basis of the training data.

The processor may extract feature data from the survey data, cluster the feature data through unsupervised machine learning, and generate the first stress classification model on the basis of the clustered feature data.

The survey data may be data in which questions, emotion factors related to the questions, and scores for the questions are recorded for each of items, and the processor may use a value obtained by summing the scores of each item for each emotion factor, a value obtained by summing all the scores of each item, and the score of each item itself as the feature data.

When a first prediction result that is output in a case in which the survey data is input to the first stress classification model matches a second prediction result that is output in a case in which the biometric data is input to the second stress classification model, the processor may generate the training data by performing a process of labeling and storing the second prediction result in the biometric data for each piece of the survey data.

The processor may receive the biometric data of the user through the communication interface, and determine whether the user is stressed on the basis of a result output by inputting the received biometric data to the personalized stress classification model.

The processor may receive reference biometric data, to which a label indicating whether the user is stressed is attached, through the communication interface, determine whether the user is stressed through the personalized stress classification model, compare a result of the determination and the label, perform a process of storing results of the comparison for each piece of the reference biometric data, and calculate accuracy of a third stress classification model on the basis of the stored results of the comparison.

According to another aspect of the present invention, there is provided a method of determining stress, which is performed by a computing device including a processor, including collecting biometric data and survey data of a user, generating a personalized stress classification model on the basis of the biometric data and the survey data, and determining whether the user is stressed using the personalized stress classification model.

According to still another aspect of the present invention, there is provided a system for determining stress, which includes a wearable device configured to detect a biometric signal related to stress from a user and generate biometric data, a user device configured to receive the biometric data transmitted from the wearable device, provide questions related to stress to the user, and generate survey data on the basis of user inputs that are input by the user in response to the questions, and a server configured to collect biometric data and survey data from the user device, generate a personalized stress classification model on the basis of the biometric data and the survey data, and determine whether the user is stressed using the personalized stress classification model.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 8 is a conceptual view showing the process of generating the third stress determination model according to the embodiment of the present invention.

DETAILED DESCRIPTION OF EXEMPLARY EMBODIMENTS

Hereinafter, embodiments of a system, apparatus, and method for determining stress according to the present invention will be described. In this process, thicknesses of lines, sizes of components, and the like shown in the accompanying drawings may be exaggerated for clarity and convenience of description. Further, some terms which will be described below are defined in consideration of functions in the present invention and meanings may vary depending on, for example, a user or operator's intentions or customs. Therefore, the meanings of these terms should be interpreted based on the scope throughout this specification.

Figure 1:
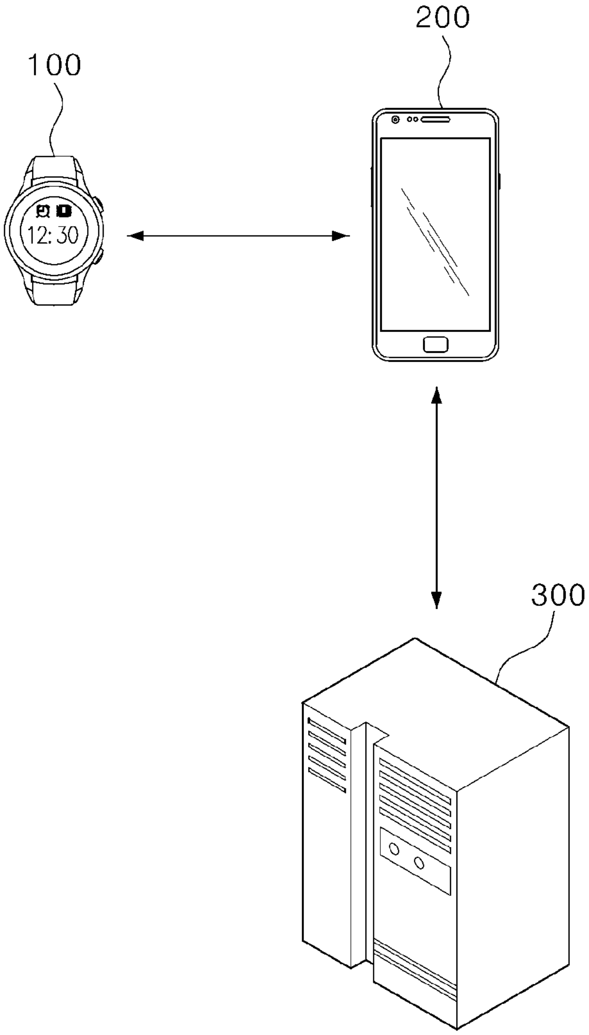
FIG. 1 is a conceptual view illustrating a system for determining stress according to an embodiment of the present invention.

FIG. 1 is a conceptual view illustrating a system for determining stress according to an embodiment of the present invention.

As illustrated in FIG. 1, the system for determining stress according to the embodiment of the present invention may include a wearable device 100, a user device 200, and a server 300.

The wearable device 100 may generate biometric data by detecting a biometric signal related to stress from a user, and transmit the generated biometric data to the user device 200 to be described below. For example, the wearable device 100 may be a smart watch equipped with a sensor for detecting at least one biometric signal, but the present invention is not limited to the above-described embodiment. The biometric data may be data for determining whether the user is physically stressed. The wearable device 100 may communicate with the user device 200 according to various types of communication methods. For example, the wearable device 100 may communicate with the user device 200 through Bluetooth.

The user device 200 may transmit the biometric data to the server 300 to be described below. For example, the user device 200 may be a smartphone, but the present invention is not limited to the above-described embodiment. Further, the user device 200 may provide questions related to stress to the user, generate survey data on the basis of user inputs that are input by the user in response to the questions, and transmit the generated survey data to the server 300. The user device 200 may communicate with the server 300 according to various types of communication methods.

TABLE 1

| Survey items | Sub-area | Strongly disagree 1 | Disagree 2 | Neutral 3 | Agree 4 | Strongly agree 5 |
|---|---|---|---|---|---|---|
| 1. I feel like my problems are not being solved and keep piling up. | Tension | | | | | |
| 2. I feel criticized or judged by others. | Depression | | | | | |
| 3. I am mentally exhausted. | Tension | | | | | |
| 4. I find it difficult to relax. | Tension | | | | | |
| 5. I am angry. | Anger | | | | | |
| 6. I have low motivation. | Depression | | | | | |
| 7. I feel on edge. | Tension | | | | | |
| 8. I want to break something. | Anger | | | | | |
| 9. I don't want to think about anything. | Depression | | | | | |

Here, the survey data is data for determining subjective (psychological) stress, and may be data in which questions, emotion factors related to the questions, and scales (scores)

for the questions are recorded for each item. Table 1 above is an exemplary example of the survey data.

Table 1 shows survey data consisting of nine survey items (parenting stress index (PSI) simplified version). The PSI simplified version is a representative survey used to evaluate Koreans' stress and consists of nine items, and each item may be given a scale rating (score) within a range of 1 to 5 points. The user may input the degree of stress in the form of a visual analog scale (VAS). The VAS is a useful tool for expressing chronic pain and is used to measure stress, fatigue, attitude, etc. and has an advantage of being able to visualize individual differences in more detail than the Likert scale.

Each item may be matched with an emotion factor (sub-area) corresponding to a question written in the corresponding item. The emotion factors may be divided into depression factors, tension factors, and anger factors. In Table 1, items 1, 3, 4, and 7 contain questions related to tension factors, items 2, 6, and 9 contain questions related to depression factors, and items 5 and 8 contain questions related to anger factors.

The user device 200 may receive a result of determining whether the user is stressed, which is transmitted from the server 300, and provide the received determination result to the user. The user device 200 may serve to relay between the user and the server 300 or to relay between the wearable device 100 and the server 300.

The server 300 may collect biometric data and survey data from the user device 200 and generate a personalized stress classification model on the basis of the collected biometric data and the collected survey data. That is, the server 300 may generate a stress model optimized for the user on the basis of the collected biometric data and the collected survey data.

The server 300 may receive the biometric data from the user device 200, and determine whether the user is stressed by inputting the received biometric data to the personalized stress classification model. The server 300 may input the biometric data of the user to the personalized stress classification model, and determine whether the user is stressed on the basis of an output value that is output from the personalized stress classification model as a result of the input.

Figure 2:
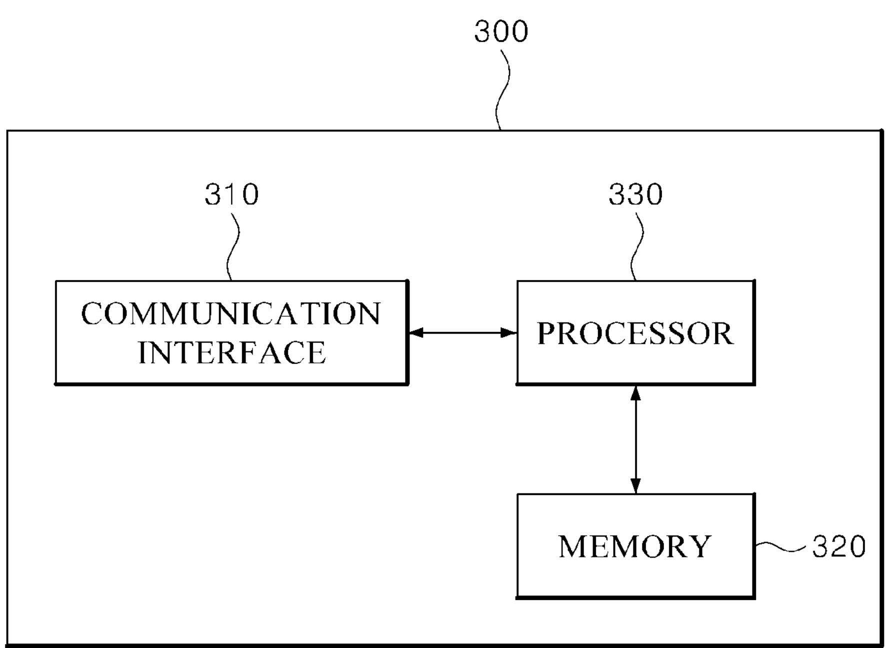
FIG. 2 is a block diagram illustrating an apparatus for determining stress according to an embodiment of the present invention.

FIG. 2 is a block diagram illustrating an apparatus for determining stress according to an embodiment of the present invention.

As illustrated in FIG. 2, the apparatus for determining stress according to the embodiment of the present invention may include a communication interface 310, a memory 320, and a processor 330. The apparatus for determining stress according to the embodiment of the present invention may correspond to the server 300 of FIG. 1.

The communication interface 310 may communicate with an external device to receive various types of information required in a process of determining whether a user is stressed, or transmit information on a result of determining whether the user is stressed. The communication interface 310 may communicate with an external device according to various types of communication methods.

In the memory 320, various types of information required while the processor 330 to be described below operates may be stored. Further, in the memory 320, various types of information calculated while the processor 330 operates may be stored. Examples of the memory 320 may include a read-only memory (ROM), a random access memory (RAM), a flash memory, a memory card, a storage medium, and/or other storage devices The processor 330 may be operatively connected to the communication interface 310 and the memory 320. The processor 330 may be implemented as a central processing unit (CPU), a micro controller unit (MCU), or a system on chip (SoC), and the processor 300 may control a plurality of hardware or software components connected to the processor 330 by driving an operating system or application, perform various types of data processing and calculations, execute at least one command stored in the memory 320, and store result data of the execution in the memory 320.

The processor 330 may collect biometric data and survey data from a user device 200 through the communication interface 310 and generate a personalized stress classification model on the basis of the biometric data and the survey data. That is, the processor 330 may generate a stress classification model optimized for the user on the basis of the collected biometric data and the collected survey data.

The processor 330 may determine whether the user is stressed using the personalized stress classification model. The processor 330 may receive the biometric data from the user device 200 through the communication interface 310, input the received biometric data to the personalized stress classification model, and determine whether the user is stressed on the basis of an output value that is output from the personalized stress classification model as a result of the input.

Figure 3:
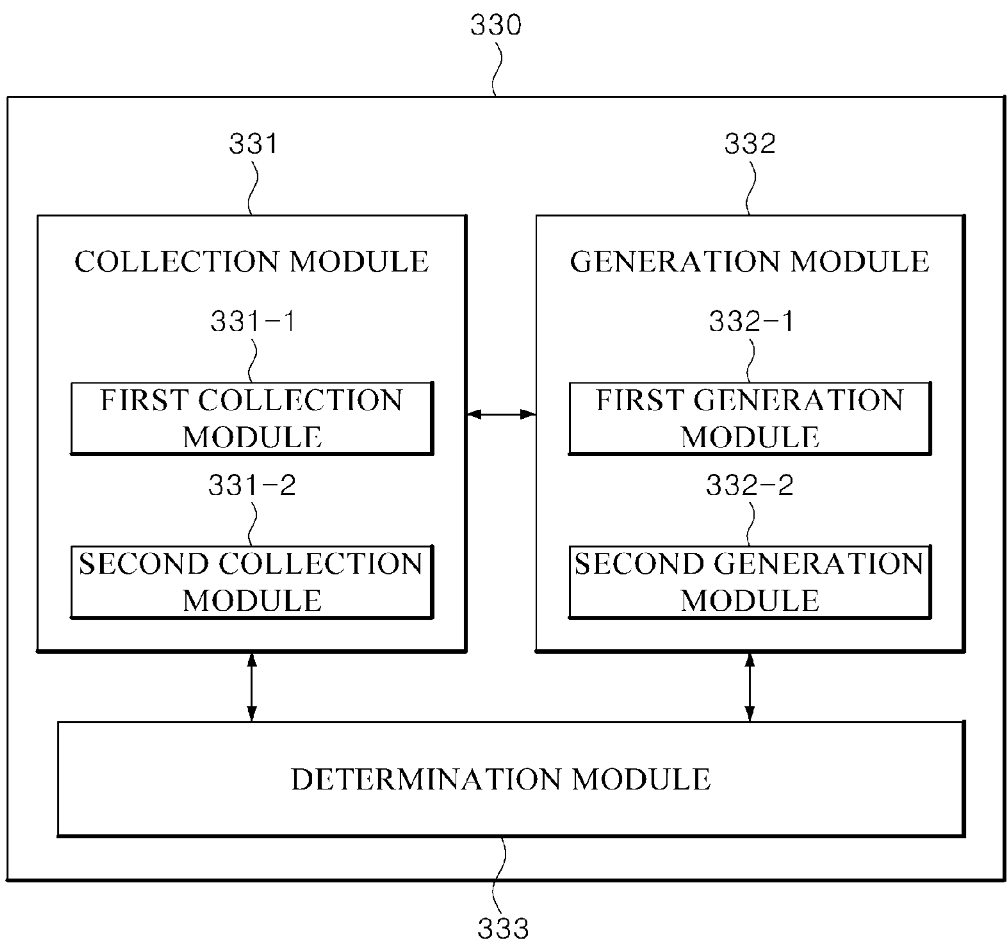
FIG. 3 is a block diagram illustrating a processor according to an embodiment of the present invention.

FIG. 3 is a block diagram illustrating the processor according to the embodiment of the present invention.

As illustrated in FIG. 3, the processor 330 may include a collection module 331, a generation module 332, and a determination module 333. The modules indicated in the present embodiment are components that perform some operations of the processor 330 that are classified according to their functions, and the operations performed by the respective modules may be understood as operations performed by the processor 330.

The collection module 331 may include a first collection module 331-1 and a second collection module 331-2. The first collection module 331-1 may collect biometric data through the communication interface 310. The second collection module 331-2 may collect survey data through the communication interface 310.

The generation module 332 may include a first generation module 332-1 and a second generation module 332-2. The first generation module 332-1 may generate a first stress classification model on the basis of the survey data collected through the second collection module 332-2. The second generation module 332-2 may generate training data from the previously collected biometric data and the previously collected survey data through a second stress classification model based on the biometric data that is pre-stored in the memory 320 and the first stress classification model, and generate a third stress classification model, which is a personalized stress classification model, on the basis of the generated training data. Here, the second stress classification model may be a stress classification model generated based on normal biometric data of the person.

The determination module 333 may receive the biometric data through the communication interface 310 and determine whether the user is stressed by inputting the received biometric data to the third stress classification model. The determination module 333 may input the biometric data to the third stress classification model, and determine whether the user is stressed on the basis of an output value of the third stress classification model that is obtained as a result of the input.

Figure 4:
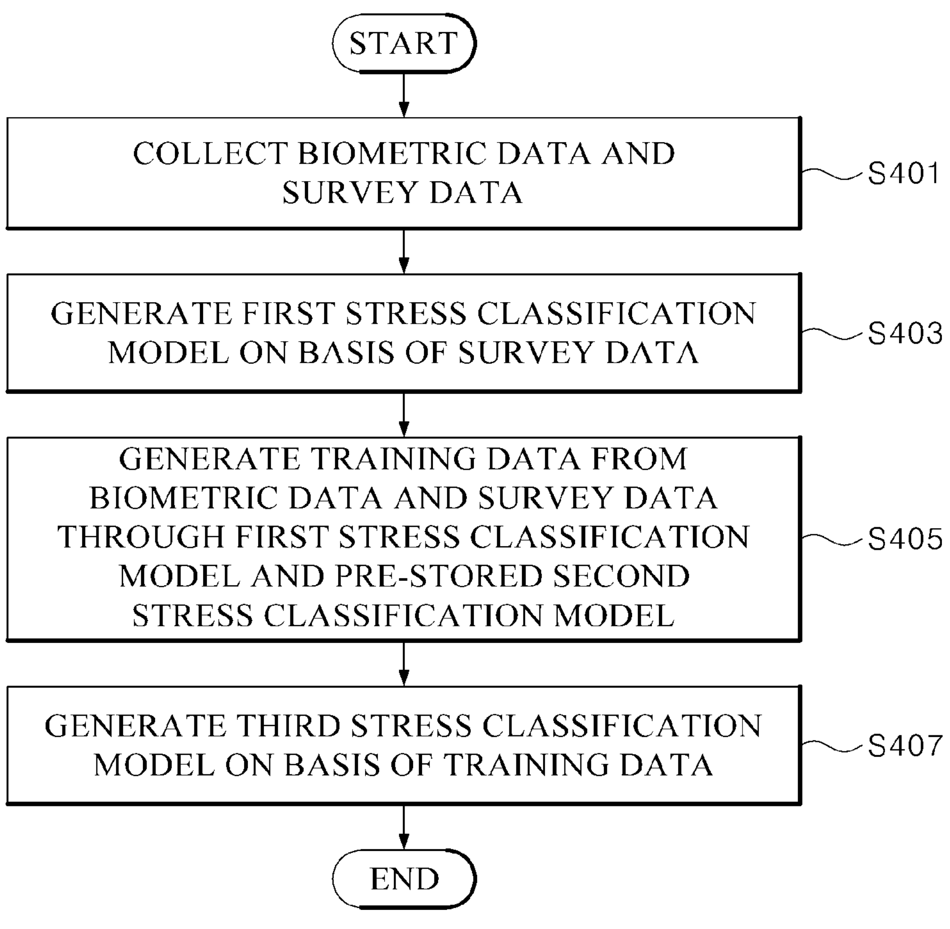
FIG. 4 is a flowchart illustrating a method of determining stress according to an embodiment of the present invention.

The determination module 333 may transmit a result of determining whether the user is stressed to the user device 200 through the communication interface 310 so that the user can check the result of determining whether the user is stressed. FIG. 4 is a flowchart illustrating a method of determining stress according to an embodiment of the present invention.

Hereinafter, a process in which the processor 330 generates a personalized stress determination model will be described with reference to FIG. 4. Some processes described below may be performed in an order different from the order described below or may be omitted.

First, the processor 330 may collect biometric data and survey data from a user device 200 through a communication interface 310 (S401).

Subsequently, the processor 330 may generate a first stress classification model on the basis of the collected survey data (S403). The processor 330 may generate the first stress classification model from the survey data through unsupervised machine learning.

Subsequently, the processor 330 may generate training data from the previously collected biometric data and the previously collected survey data through a second stress classification model based on the biometric data that is pre-stored in a memory 320 and the first stress classification model (S405).

In order to generate a stress classification model optimized for a user, biometric data obtained from the user should be used as training data for a stress classification model. However, since the biometric data obtained from the user is not labeled, it is necessary to label the biometric data in order to use the biometric data obtained from the user as the training data for the stress classification model. Therefore, the processor 330 may perform labeling on the biometric data by utilizing both the first stress classification model, which is a stress classification model based on survey data, and the second stress classification model, which is a stress classification model based on biometric data. As described above, in the present embodiment, the training data may be generated by reflecting psychological information of the user, and the stress classification model may be optimized for the user by generating the stress classification model through the training data.

Subsequently, the processor 330 may generate a third stress classification model, which is a personalized stress classification model, on the basis of the training data (S407). The processor 330 may generate the third stress classification model from the training data through supervised machine learning.

Figure 5:
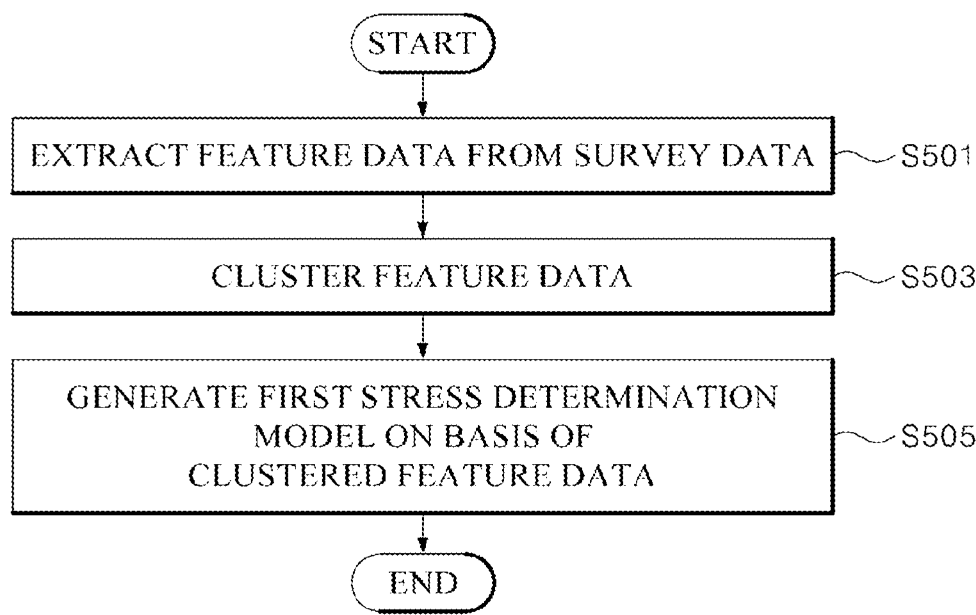
FIG. 5 is a flowchart illustrating a process of generating a first stress determination model according to an embodiment of the present invention.
Figure 6:
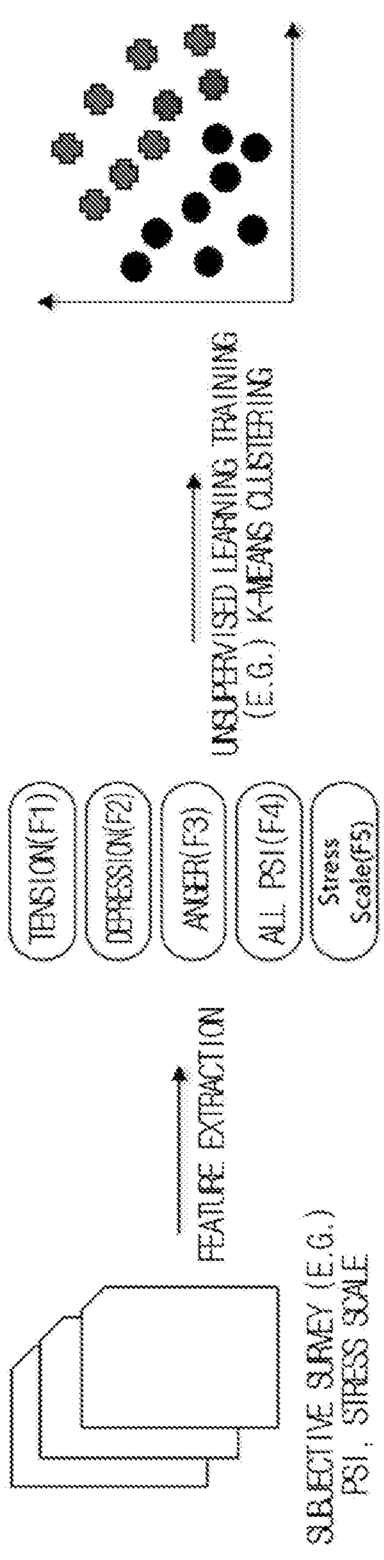
FIG. 6 is a conceptual view showing the process of generating the first stress determination model according to the embodiment of the present invention.

FIG. 5 is a flowchart illustrating a process of generating a first stress determination model according to an embodiment of the present invention, and FIG. 6 is a conceptual view showing the process of generating the first stress determination model according to the embodiment of the present invention.

Hereinafter, a process in which the processor 330 generates the first stress determination model will be described with reference to FIGS. 5 and 6.

First, the processor 330 may extract feature data from survey data (S501). In this case, the processor 330 may use a value obtained by summing scores of items for each of emotion factors, a value obtained by summing all the scores of the items, and the score of each item itself as feature data.

For example, referring to Table 1, the processor 330 may calculate a value (i.e., a value obtained by summing scores described in items 1, 3, 4, and 7) obtained by summing scores matched with items related to tension factors, a value (i.e., a value obtained by summing scores described in items 2, 6, and 9) obtained by summing scores matched with items related to depression factors, a value (i.e., a value obtained by summing scores described in items 5 and 8) obtained by summing scores matched with items related to anger factors, and a value (i.e., a value obtained by summing the scores described in items 1 to 9) obtained by summing all the scores matched with the items, and use the values as the feature data.

Subsequently, the processor 330 may cluster the feature data through unsupervised machine learning (S503). The processor 330 may cluster the feature data using a k-means clustering algorithm. For example, the processor 330 may set k=2 and classify a stress state of the user in the form of a binary state (stress/non-stress). The value of k may be changed according to the designer's intention. When the value of k is set to a value greater than 2, the stress state of the user may be further subdivided.

Subsequently, the processor 330 may generate a first stress determination model on the basis of the clustered feature data (S505). That is, the processor 330 may label the feature data (survey data) according to a result of the clustering and generate the first stress determination model using the labeled feature data.

Figure 7:
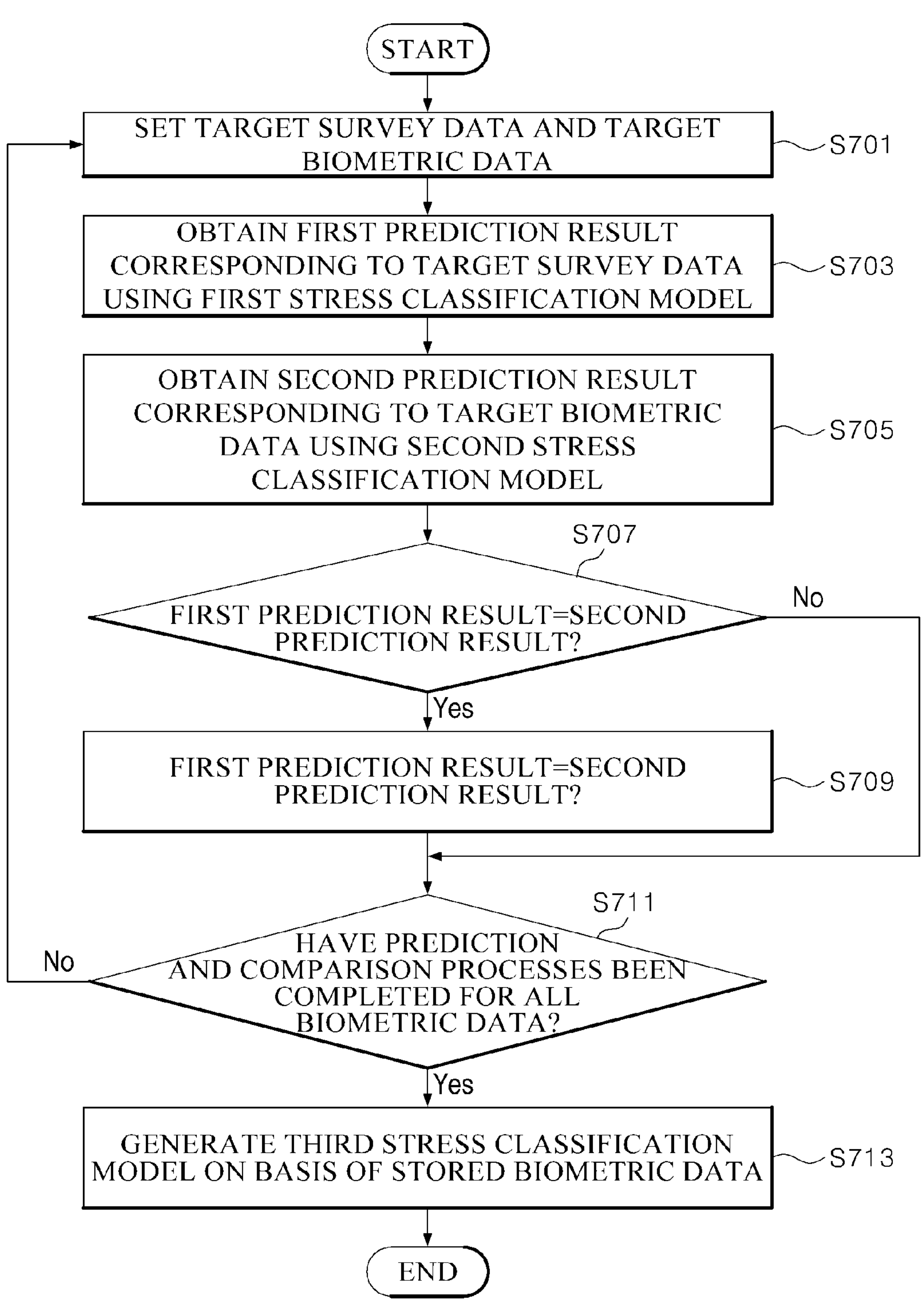
FIG. 7 is a flowchart illustrating a process of generating a third stress determination model according to an embodiment of the present invention.

FIG. 7 is a flowchart illustrating a process of generating a third stress determination model according to an embodiment of the present invention, and FIG. 8 is a conceptual view showing the process of generating the third stress determination model according to the embodiment of the present invention.

Hereinafter, a process in which the processor 330 generates the third stress determination model will be described with reference to FIGS. 7 and 8.

First, the processor 330 may set one piece of the collected survey data as target survey data, and set biometric data corresponding to the set target survey data as target biometric data (S701). Here, the biometric data corresponding to the survey data may be biometric data generated at the same time point as a time point at which the survey data is generated.

Subsequently, the processor 330 may obtain a first prediction result corresponding to the target survey data using a first stress classification model (S703). When the target survey data is input to the first stress classification model, the processor 330 may obtain an output value output from the first stress classification model as the first prediction result.

Subsequently, the processor 330 may obtain a second prediction result corresponding to the target biometric data using a second stress classification model (S705). When the target biometric data is input to the second stress classification model, the processor 330 may obtain an output value output from the second stress classification model as the second prediction result.

Subsequently, the processor 330 may determine whether the first prediction result matches the second prediction result (S707).

When it is determined that the first prediction result matches the second prediction result, the processor 330 may label the second prediction result in the target biometric data and store the labeled target biometric data in a memory 320 (S709). When it is determined that the first prediction result matches the second prediction result, the processor 330 may determine the corresponding biometric data as reliable data and store the corresponding biometric data in order to use it as training data. On the other hand, when it is not determined that the first prediction result matches the second prediction result, the processor 330 may determine the corresponding biometric data as unreliable data and may not store the corresponding biometric data.

Subsequently, the processor 330 may determine whether the prediction and comparison process has been completed for all the collected biometric data (S711). That is, the processor 330 may determine whether operations S701 to S707 have been performed on all the collected biometric data.

When it is not determined that the prediction and comparison processes have been completed for all the collected biometric data, the processor 330 may return to operation S701 and perform the above-described processes on the biometric data that has not been selected as the target biometric data.

On the other hand, when it is determined that the prediction and comparison processes have been completed for all the collected biometric data, the processor 330 may generate a third stress classification model, which is a personalized stress classification model, by performing supervised machine learning on the basis of the labeled biometric data stored in a memory 320 (S713).

Figure 9:
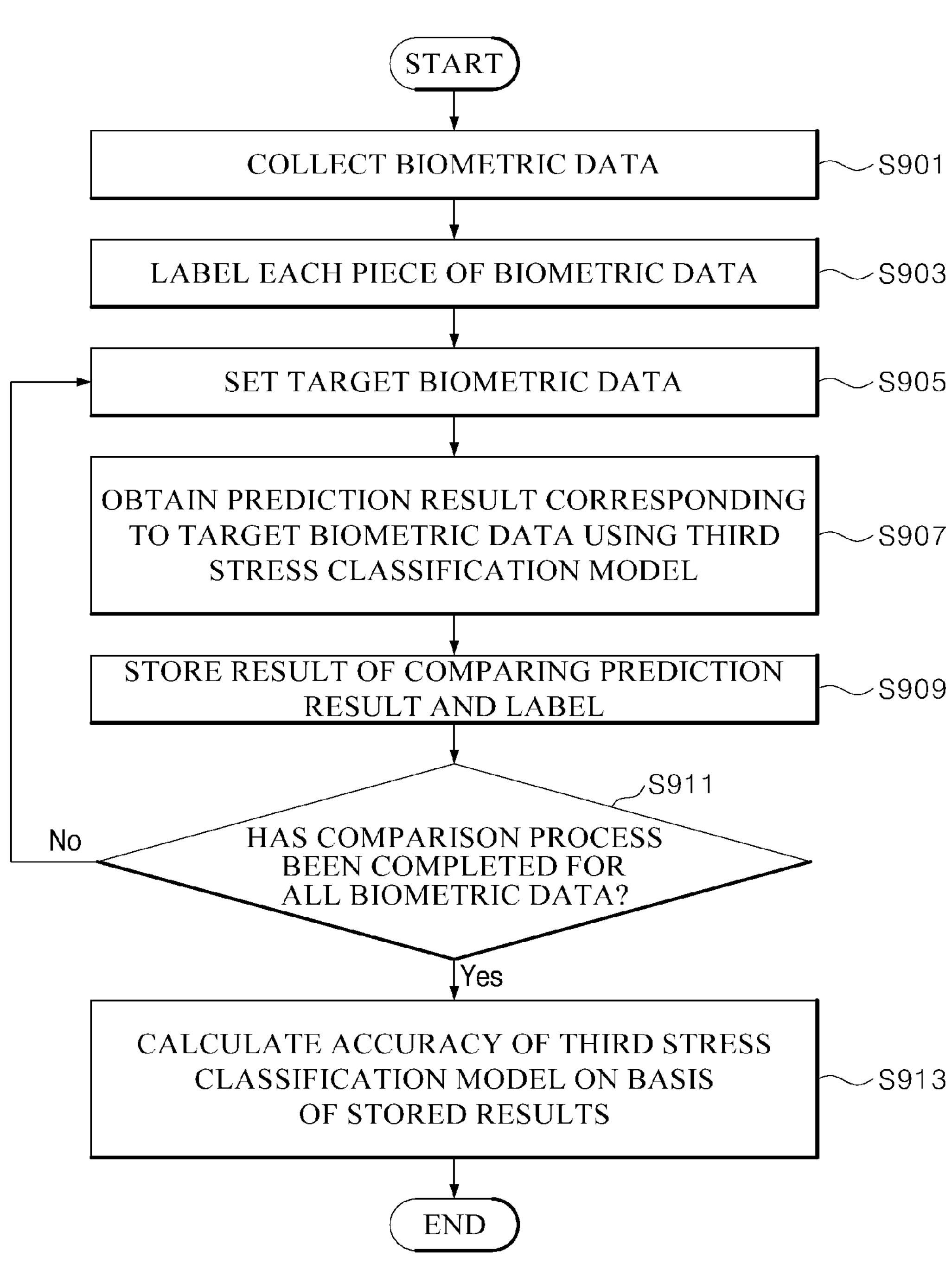
FIG. 9 is a flowchart illustrating a process of evaluating a third stress determination model according to an embodiment of the present invention.

FIG. 9 is a flowchart illustrating a process of evaluating a third stress determination model according to an embodiment of the present invention.

Hereinafter, a process in which the processor 330 evaluates the third stress determination model will be described with reference to FIG. 9.

First, the processor 330 may collect biometric data that is generated in a stress environment and biometric data (reference biometric data) that is generated in a non-stress environment, through the communication interface 310 (S901). Here, the stress environment is an environment that causes stress, and may be, for example, an environment in which a paced auditory serial addition test (PASAT) is performed. The PASAT is a test developed to measure a change in cognitive function caused by traumatic brain injury, and may cause a cognitive load on a person. In the PASAT, when a single-digit number is output every 2 seconds, a person calculates a value obtained by adding the sum of the previous number and the current number through mental arithmetic and says it out loud. Meanwhile, the non-stress environment is an environment that does not cause stress, and may be, for example, an environment in which comfortable rest is provided.

Subsequently, the processor 330 may label each piece of the collected biometric data (S903). The processor 330 may label each piece of the biometric data generated in the stress environment with a first label (stress) and label each piece of the biometric data generated in the non-stress environment with a second label (non-stress).

Subsequently, the processor 330 may set one piece of the collected biometric data as target biometric data (S905).

Subsequently, the processor 330 may obtain a prediction result corresponding to the target biometric data using a third stress classification model (S907). That is, the processor 330 may input the target biometric data to the third stress classification model and obtain an output value of the third stress classification model.

Subsequently, the processor 330 may determine whether the prediction result of the target biometric data matches the label of the target biometric data, and store information on a result of the determination in the memory 320 (S909). That is, the processor 330 may determine whether the stress predicted through the third stress classification model matches a result of actually checking whether or not there is stress.

Subsequently, the processor 330 may determine whether the process of comparing the prediction result with the label has been completed for all the collected biometric data (S911). That is, the processor 330 may determine whether operations S905 to S909 have been performed on all the collected biometric data.

When it is not determined that the process of comparing the prediction result with the label has been completed for all the collected biometric data, the processor 330 may return to operation S905 and perform the above-described processes on the biometric data that has not been selected as the target biometric data.

When it is determined that the process of comparing the prediction result with the label has been completed for all the collected biometric data, the processor 330 may calculate the accuracy of the third stress classification model on the basis of the information stored in the memory 320 (S913). The processor 330 may calculate a ratio of the biometric data whose label matches the prediction results to all the collected biometric data to calculate the accuracy of the third stress classification model.

As described above, in the present invention, by determining whether a user is stressed and providing a result of the determination to the user, it is possible to support the user in efficiently managing stress, and furthermore, it is possible to support the user to lead a healthy daily life. Further, in the present invention, a stress classification model optimized for a user can be generated using physical and psychological information collected from the user, and the optimized stress classification model can be used to determine whether the user is stressed, thereby improving the accuracy of stress determination for the user.

In the system, apparatus, and method for determining stress according to the present invention, by determining whether a user is stressed and providing a result of the determination to the user, it is possible to support the user in efficiently managing stress, and furthermore, it is possible to support the user to lead a healthy daily life.

Further, in the system, apparatus, and method for determining stress according to the present invention, a stress classification model optimized for a user can be generated using physical and psychological information collected from the user, and the optimized stress classification model can be used to determine whether the user is stressed, thereby improving the accuracy of stress determination for the user.

While the present invention has been described with reference to the embodiment illustrated in the accompanying drawings, the embodiment should be considered in a descriptive sense only, and it should be understood by those skilled in the art that various alterations and other equivalent embodiments may be made. Therefore, the scope of the present invention should be defined by only the following claims.

What is claimed is:

1. An apparatus for determining stress, comprising:

a communication interface; and a processor connected to the communication interface, wherein the processor is configured to:

collect biometric data and survey data of a user through the communication interface, wherein the biometric data of the user is used to obtain information indicating a physical stress of the user, and wherein the survey data of the user is used to obtain information indicating psychological stress of the user;

generate a first stress classification model based on the survey data;

generate training data from the biometric data and the survey data using the first stress classification model and a pre-stored biometric data-based second stress classification model generated based on biometric data acquired from a non-stressed state, by:

obtaining a first prediction result corresponding to the psychological stress of the user by inputting target survey data to the first stress classification model;

obtaining a second prediction result corresponding to the physical stress of the user by inputting target biometric data corresponding in time to the target survey data to the second stress classification model; and when the first prediction result matches the second prediction result, determining the target biometric data as reliable data, labeling the target biometric data with the second prediction result and storing the labeled target biometric data as the training data, and when the first prediction result does not match the second prediction result, not storing the target biometric data as the training data, generate a personalized stress classification model based on the training data by performing supervised machine learning on the stored labeled target biometric data, and determine whether the user is stressed using the personalized stress classification model.

2. The apparatus of claim 1, wherein the processor extracts feature data from the survey data, clusters the feature data through unsupervised machine learning, and generates the first stress classification model based on the clustered feature data.

3. The apparatus of claim 2, wherein the survey data is data in which questions, emotion factors related to the questions, and scores for the questions are recorded for each of items, and the processor uses a value obtained by summing the scores of each item for each emotion factor, a value obtained by summing all the scores of each item, and the score of each item itself as the feature data.

4. The apparatus of claim 1, wherein the processor receives the biometric data of the user through the communication interface, and determines whether the user is stressed based on a result output by inputting the received biometric data to the personalized stress classification model.

5. The apparatus of claim 1, wherein the processor receives reference biometric data, to which a label indicating whether the user is stressed is attached, through the communication interface, determines whether the user is stressed through the personalized stress classification model, compares a result of the determination and the label, performs a process of storing results of the comparison for each piece of the reference biometric data, and calculates accuracy of a third stress classification model based on the stored results of the comparison.

6. A method of determining stress, which is performed by a computing device including a processor, comprising:

collecting biometric data and survey data of a user, wherein the biometric data of the user is used to obtain information indicating a physical stress of the user, and wherein the survey data of the user is used to obtain information indicating psychological stress of the user;

generating a first stress classification model based on the survey data;

generating training data from the biometric data and the survey data using the first stress classification model and a pre-stored biometric data-based second stress classification model generated based on biometric data acquired from a non-stressed state, by:

obtaining a first prediction result corresponding to the psychological stress of the user by inputting target survey data to the first stress classification model;

obtaining a second prediction result corresponding to the physical stress of the user by inputting target biometric data corresponding in time to the target survey data to the second stress classification model; and when the first prediction result matches the second prediction result, determining the target biometric data as reliable data, labeling the target biometric data with the second prediction result and storing the labeled target biometric data as the training data, and when the first prediction result does not match the second prediction result, not storing the target biometric data as the training data, generating a personalized stress classification model based on the training data by performing supervised machine learning on the stored labeled target biometric data; and determining whether the user is stressed using the personalized stress classification model.

7. The method of claim 6, wherein the generating of the first stress classification model includes:

extracting feature data from the survey data;

clustering the feature data through unsupervised machine learning; and generating the first stress classification model based on the clustered feature data.

8. The method of claim 7, wherein the survey data is data in which questions, emotion factors related to the questions, and scores for the questions are recorded for each of items, and in the extracting of the feature data, a value obtained by summing the scores of each item for each emotion factor, a value obtained by summing all the scores of each item, and the score of each item itself as the feature data are used.

9. The method of claim 6, wherein the determining of whether the user is stressed includes:

receiving the biometric data of the user; and determining whether the user is stressed based on a result output by inputting the received biometric data to the personalized stress classification model.

10. The method of claim 6, further comprising receiving reference biometric data to which a label indicating whether the user is stressed is attached;

determining whether the user is stressed through the personalized stress classification model, comparing a result of the determination and the label, and performing a process of storing results of the comparison for each piece of the reference biometric data; and calculating accuracy of a third stress classification model based on the stored results of the comparison.

11. A system for determining stress, comprising:

a wearable device configured to detect a biometric signal related to stress from a user and generate biometric data;

a user device configured to receive the biometric data transmitted from the wearable device, provide questions related to stress to the user, and generate survey data based on user inputs that are input by the user in response to the questions; and a server configured to collect biometric data and survey data from the user device, generate a first stress classification model based on the survey data, generate training data from the biometric data and the survey data using the first stress classification model and a pre-stored biometric data-based second stress classification model, by obtaining a first prediction result by inputting target survey data to the first stress classification model, obtaining a second prediction result by inputting target biometric data corresponding in time to the target survey data to the second stress classification model, and when the first prediction result matches the second prediction result, determining the target biometric data as reliable data, labeling the target biometric data with the second prediction result and storing the labeled target biometric data as the training data, and when the first prediction result does not match the second prediction result, not storing the target biometric data as the training data, generate a personalized stress classification model based on the training data by performing supervised machine learning on the stored labeled target biometric data, and determine whether the user is stressed using the personalized stress classification model, wherein the biometric data of the user is used to obtain information indicating a physical stress of the user, and wherein the survey data of the user is used to obtain information indicating psychological stress of the user, wherein the second stress classification model is generated based on biometric data acquired from a non-stressed state, wherein the first prediction result corresponds to the psychological stress of the user, and wherein the second prediction result corresponds to the physical stress of the user.

12. The system of claim 11, wherein the server extracts feature data from the survey data, clusters the feature data through unsupervised machine learning, and generates the first stress classification model on the basis of the clustered feature data.

13. The system of claim 12, wherein the survey data is data in which questions, emotion factors related to the questions, and scores for the questions are recorded for each of items, and the server uses a value obtained by summing the scores of each item for each emotion factor, a value obtained by summing all the scores of each item, and the score of each item itself as the feature data.

14. The system of claim 11, wherein the server receives the biometric data of the user from the user device, and determines whether the user is stressed based on a result output by inputting the received biometric data to the personalized stress classification model.

* * * * *